United States Patent
Kelly

(10) Patent No.: US 6,586,636 B2
(45) Date of Patent: Jul. 1, 2003

(54) ALDOL CONDENSATION

(75) Inventor: Gordon James Kelly, Darlington (GB)

(73) Assignee: Imperial Chemical Industries PLC, London (GB)

(*) Notice: Subject to any disclaimer, the term of this patent is extended or adjusted under 35 U.S.C. 154(b) by 333 days.

(21) Appl. No.: 09/861,529

(22) Filed: May 22, 2001

(65) Prior Publication Data

US 2001/0044558 A1 Nov. 22, 2001

Related U.S. Application Data

(63) Continuation of application No. PCT/GB99/03534, filed on Oct. 25, 1999.

(30) Foreign Application Priority Data

Nov. 25, 1998 (GB) ............................................. 9825703
Jan. 22, 1999 (GB) ............................................. 9901324

(51) Int. Cl.⁷ ............................................. C07C 45/72
(52) U.S. Cl. ....................... 568/463; 568/459; 568/461; 568/464; 568/881; 568/885
(58) Field of Search ................................. 568/459, 461, 568/463, 464, 881, 885

(56) References Cited

U.S. PATENT DOCUMENTS

| 4,942,258 A | 7/1990 | Smith |
| 5,144,089 A | 9/1992 | Arena et al. |
| 5,334,770 A | * 8/1994 | Ueda et al. .................. 568/463 |

FOREIGN PATENT DOCUMENTS

| FR | 870 204 | 3/1942 |
| GB | 731 917 | 6/1955 |
| GB | 1 458 129 | 12/1976 |

OTHER PUBLICATIONS

Tsuji et al., "Self–Condensation of N–Butyraldehyde Over Solid Base Catalysts", Journal of Catalysis, U.S. Academic Press, vol. 148, No. 2, pp 759–770 (1994).

* cited by examiner

*Primary Examiner*—Sreeni Padmanabhan
(74) *Attorney, Agent, or Firm*—Pillsbury Winthrop LLP

(57) ABSTRACT

Production of unsaturated aldehydes by the aldol condensation of straight chain aldehydes, e.g. butyraldehyde, by contacting the aldehyde in the vapour phase with a particulate catalyst comprising at least one basic alkali metal compound supported on an inert substrate at a temperature above 175° C.

17 Claims, No Drawings

ALDOL CONDENSATION

This is a Continuation of International application No. PCT/GB99/03534 filed Oct. 25, 1999 which designated the U.S., and that International application was published under PCT Article 21(2) in English.

This invention relates to aldol condensation and in particular to the condensation of straight chain aldehydes such as propanal, butanal, or hexanal.

The aldol condensation of propanal or butanal is an important step in the production of oxo alcohols such as 2-ethyl hexanol. For example, as described in GB 1462328, butanal is typically condensed using an aqueous caustic catalyst at a temperature of the order of 80 to 140° C. to give 2-ethyl hexenal which is then hydrogenated to 2-ethyl hexanol.

We have found that the condensation can be effected in the gaseous phase using a solid base catalyst thereby avoiding the need for aqueous caustic solutions with their consequent handling and effluent disposal problems.

U.S. Pat. No. 5,144,089, U.S. Pat. No. 5,254,743 and U.S. Pat. No. 5,258,558 describe the hydrogenation of butanal in the liquid phase using fixed bed catalysts based on magnesia-containing compositions. However it is desirable to devise a gas phase process since such a process would be easier to back integrate into the gas phase OXO hydroformylation process that is used to produce aldehydes such as butanal and so energy savings could be achieved by eliminating an aldehyde vaporisation process. It would appear from these U.S. patents that the magnesia based catalysts require activation by heating at high temperatures in an inert atmosphere before use. Such a pre-treatment step is undesirable. Also it would be desirable to provide a process employing catalysts that may be more selective than the aforesaid magnesia-containing catalysts.

The aforementioned U.S. patents also mention the use of fixed bed catalysis using sodium on alumina or potassium on graphite. It is believed that this is a reference to the type of catalysts described by Pines et al in "Base-catalysed reactions of hydrocarbons and related compounds", Academic Press, 1977, pages 18–20 in which the alkali metal was in the elemental form and which were generally used at low temperatures for the liquid phase reactions. These catalysts are unsuitable for aldol condensations since they would be rapidly de-activated by the water produced in the condensation reaction. Also such catalysts are liable to lead to low product selectivity.

U.S. Pat. No. 5,453,412 and U.S. Pat. No. 5,498,587 describe the hydrogenation of butanal using certain copper catalysts containing sodium oxide at relatively low temperatures, below 160° C. We have found that higher temperatures are necessary in order to effect aldol condensation with solid base catalysts. Thus under the conditions described in the Examples of those U.S. patents, essentially no aldol condensation took place.

Accordingly the present invention provides a process for the production of unsaturated aldehydes by the aldol condensation of straight chain aldehydes by contacting the aldehyde in the vapour phase with a particulate catalyst comprising at least one basic alkali metal compound supported on an inert substrate at a temperature above 175° C.

Suitable catalysts are basic sodium, potassium, or cesium compounds such as oxides hydroxides or carbonates supported on a material such as carbon, silica, alumina, a clay, silicalite or a zeolite. Preferred catalysts are alkali metal compounds supported on silica, especially potassium or sodium supported on silica. The potassium and sodium catalysts appear to have high activity and are the most selective. The catalyst preferably contains 0.1 to 25%, preferably 0.4 to 18%, by weight of the alkali metal.

The support preferably is in the form of particles having maximum and minimum dimensions in the range 0.5 to 10 mm, preferably 1 to 4 mm, and having a BET surface area in the range 50 to 500 m$^2$/g. The catalyst is preferably made by impregnating the support particles with an aqueous solution of an alkali metal compound that is basic or decomposes to a basic compound upon heating, for example an alkali metal hydroxide, acetate, oxalate, nitrate or carbonate, followed by drying and calcination if necessary to effect decomposition to a basic compound.

The reaction is effected at temperatures above 175° C., particularly above 200° C., and preferably below 450° C., particularly in the range 200 to 350° C. As the temperature increases the activity increases but the selectivity tends to decrease, often with the production of hydrogenated products.

The aldehyde is preferably a straight chain aldehyde containing 2 to 8 carbon atoms, preferably, propanal, butanal, or hexanal.

After a period of operation, the activity of the catalyst tends to decrease through the deposition of carbon as a result of side reactions. The catalyst may be periodically regenerated by burning off the carbon by heating in an oxygen-containing atmosphere, e.g. air or oxygen or air diluted with an inert gas such as nitrogen. The catalyst may be disposed as a fixed bed or a fluidised bed may be employed. In the latter case a portion of the catalyst may be continuously withdrawn and regenerated and returned to the reaction zone.

The main product of the condensation is an unsaturated aldehyde, e.g. 2-ethyl hex-2-enal in the case of condensation of butanal, or 2-butyl oct-2-enal in the case of hexanal. Often it is desired to hydrogenate the product to the corresponding alcohol, e.g. 2-ethyl hexanol, or 2-butyl octanol. This may be effected by passing the products, possibly after separation of the starting aldehyde that has not reacted, together with hydrogen, through a bed of a suitable hydrogenation catalyst, such as copper or a platinum group metal, on a suitable support. The temperature of the hydrogenation is effected will often be below that used for the aldol condensation. The reaction mixture from the aldol condensation may be cooled to the desired hydrogenation temperature by addition of a suitable quench gas, such as cool hydrogen.

In some cases it may be desired to produce a mixture of the alcohol resulting from hydrogenation of the aldol condensation and the alcohol resulting from hydrogenation of the feed aldehyde. For example it may be desired to produce a mixture of 2-ethyl hexanol and butanol. Where this is desired, separation of the condensation product from the feed aldehyde prior to hydrogenation will generally not be necessary. Indeed in some cases it may be desirable to provide a bypass so that part of the feed aldehyde may bypass the aldol condensation step. In this case, the bypass aldehyde may be cooled so that it may be used as part or all of the quench gas. Where such a bypass is employed, variation of the amount of bypassing aldehyde may be used to control the relative proportions of the products, e.g. to compensate for declining activity of the base catalyst.

As indicated above, the primary product from the condensation is the unsaturated aldehyde, e.g. 2-ethyl hex-2-enal or 2-butyl oct-2-enal. In some cases, the desired product is not the corresponding alcohol but is the corresponding saturated aldehyde, e.g. 2-ethyl hexanal or 2-butyl octanal. The unsaturated aldehyde may be hydrogenated to the saturated aldehyde using a hydrogenation catalyst, such as palladium, that effects hydrogenation of the carbon—carbon double bond but does not effect hydrogenation of the carbonyl group.

In some cases it may be possible to effect the condensation and hydrogenation in a single stage by formulating the base catalyst also to have the appropriate hydrogenation activity and co-feeding hydrogen with the aldehyde to the reaction zone. Such a base/hydrogenation catalyst may be a mixture of separate particles of base and hydrogenation catalyst, or may be particles of the support impregnated with both a base and a material having hydrogenation activity. However, it has been found that where the condensation and hydrogenation is effected in a single stage, e.g. by the use of a catalyst having both the condensation and hydrogenation activity, the condensation activity of the catalyst may decrease relatively rapidly. Therefore it is preferred to effect such condensation and hydrogenation in separate stages, e.g. by using a bed of the condensation catalyst, followed by a bed of the hydrogenation catalyst. In this case it is preferred that the condensation catalyst is free from components, such as copper, and Group VIII metals, giving hydrogenation activity.

The invention is illustrated by the following examples.

EXAMPLES 1–8

A series of catalysts were made by impregnating a gel silica in the form of spheres of diameter in the range 2–4 mm having a purity of over 99%, a total surface area of about 300–350 m²/g, and a pore volume of 1.04 cm³/g with 76% of the pore volume provided by pores having a diameter in the range 7–23 nm with aqueous solutions of alkali metal nitrates and calcining at 450° C. for 3 hours to obtain catalysts containing various loadings of the alkali metal oxide. The catalysts were tested for the aldol condensation of butanal at varying temperatures by passing a mixture of butanal at a liquid flow rate of 0.33 ml/min entrained in nitrogen at a gas flow rate of 250 ml/min through a fixed bed of 10 ml of the catalyst at a pressure of 3 bar gauge. The products were analysed by gas chromatography-mass spectroscopy. In these examples, the conversion is the number of moles of n-butanal reacted as a percentage of the number of moles of n-butanal in the feed, and the selectivity is two times the number of moles of aldol condensation products as a percentage of the number of moles of n-butanal reacted where the aldol condensation products are cis-2-ethyl hex-2-enal and trans-2-ethyl hex-2-enal (which were the major aldol condensation products), and the hydrogenated derivatives thereof, i.e. 2-ethyl hexanal and 2-ethyl hexanol.

In Examples 1–3 different alkali metals were employed with the catalyst containing 4% by weight of the alkali metal as alkali metal oxide. In Examples 4 and 5 different amounts of alkali metal were used so that the molar loading was the same (0.3 mmoles per g of catalyst) as in Example 1. In Example 6, Example 2 was repeated with a higher loading of potassium. In Examples 1–6 the aldol condensation was effected at 200° C.

In Examples 7–8, the catalyst of Example 5 was tested at different temperatures to show the effect of temperature on selectivity.

The results are shown in the following table.

| Example | Alkali Type | Alkali Weight (%) | Temperature (° C.) | Conversion (%) | Selectivity (%) |
|---|---|---|---|---|---|
| 1 | Cs | 4.0 | 200 | 47.9 | 79.2 |
| 2 | K | 4.0 | 200 | 46.0 | 79.8 |
| 3 | Na | 4.0 | 200 | 50.2 | 87.5 |
| 1 | Cs | 4.0 | 200 | 47.9 | 79.2 |
| 4 | K | 1.2 | 200 | 41.8 | 83.3 |
| 5 | Na | 0.7 | 200 | 38.8 | 85.9 |
| 4 | K | 1.2 | 200 | 41.8 | 83.3 |
| 2 | K | 4.0 | 200 | 46.0 | 79.8 |
| 6 | K | 10.0 | 200 | 12.5 | 49.0 |
| 5 | Na | 0.7 | 200 | 38.8 | 85.9 |

-continued

| Example | Alkali Type | Alkali Weight (%) | Temperature (° C.) | Conversion (%) | Selectivity (%) |
|---|---|---|---|---|---|
| 7 | Na | 0.7 | 250 | 49.8 | 81.8 |
| 8 | Na | 0.7 | 300 | 61.0 | 41.5 |

EXAMPLE 9

The testing of the catalyst of Example 2 at 200° C. was continued for several days to ascertain the effect of time on line on the conversion and selectivity. The results are shown in the following table.

| Time on line (days) | Conversion (%) | Selectivity (%) |
|---|---|---|
| 1 | 46.0 | 79.8 |
| 2 | 32.2 | 80.7 |
| 3 | 24.8 | 72.7 |
| 4 | 22.2 | 70.2 |
| 5 | 20.9 | 62.5 |

Testing of the catalyst of Example 3 in the same manner gave a similar profile of the change of conversion and selectivity with time.

EXAMPLES 10–15

In these examples, the aldol condensation of n-butanal followed by hydrogenation was effected using a 3 ml bed of the catalyst of Example 3 crushed to a particle size of 0.6 to 1 mm, followed by a 3 ml bed of a copper oxide/zinc oxide hydrogenation catalyst made by co-precipitation and containing 35% by weight of copper oxide. This hydrogenation catalyst was likewise crushed to a particle size of 0.6 to 1 mm. Before commencing the testing, the hydrogenation catalyst was reduced in a current of dilute hydrogen (10% by volume of hydrogen in nitrogen) at 160° C. over a period of 24 hours.

n-Butanal and hydrogen were fed through the sodium oxide on silica catalyst which was maintained at 350° C. and then the reaction products fed through the hydrogenation catalyst which was maintained at 130° C. A series of experiments were performed with different feed rates and pressures as set out in the following table. In all the experiments, the feed was continued for a period of 24 hours and the reaction products monitored.

In all cases all the n-butanal reacted, to form a mixture of n-butanol and 2-ethyl hexanol. In the following table the relative proportions of these products is quoted as EOH/BOH=moles of 2-ethyl hexanol formed/moles of n-butanol formed×100%

| Example | Pressure (bar) | H₂ flow rate (ml/min) | n-butanal flow rate (ml liquid/min) | EOH/BOH (%) |
|---|---|---|---|---|
| 10 | 3 | 80 | 0.05 | 14.9 |
| 11 | 5 | 80 | 0.05 | 19.9 |
| 12 | 7 | 80 | 0.05 | 23.3 |
| 13 | 5 | 80 | 0.025 | 17.3 |
| 14 | 5 | 40 | 0.025 | 21.5 |
| 15 | 5 | 100 | 0.025 | 9.8 |

It is seen that the proportion of 2-ethyl hexanol increases as the pressure increases and as the hydrogen feed rate is decreased. At a constant hydrogen to n-butanal ratio, the proportion of 2-ethyl hexanol increases as the n-butanal feed rate decreases, i.e. as the space velocity decreases.

EXAMPLE 16

In this example, the aldol condensation of n-butanal was effected using a 3 ml bed of the catalyst of Example 3 crushed to a particle size of 0.6 to 1 mm.

n-Butanal (0.05 ml liquid/min) and hydrogen (42 ml/min) at a pressure of 7 bar gauge were continuously passed through to the catalyst which was maintained at 350° C. After various times on-line, samples of the products were analysed by gas chromatography.

After 22 hours on-line, the hydrogen flow rate was decreased to 21 ml/min. After 46 hours on-line, the temperature was increased to 400° C., and then to 450° C. after a total of 70 hours on-line. After a total of 72 hours on-line the experiment was stopped and the catalyst analysed and found to contain 10.6% by weight of carbon. The results are shown in the following table.

The selectivity to "aldol" is two times the number of moles of aldol condensation products as a percentage of the number of moles of n-butanal reacted where the aldol condensation products are cis-2-ethyl hex-2-enal and trans-2-ethyl hex-2-enal and the hydrogenated derivatives thereof, i.e. 2-ethyl hexanal and 2-ethyl hexanol.

"enal"/"aldol" is the sum of the number of moles of cis-2-ethyl hex-2-enal and trans-2-ethyl hex-2-enal as a percentage of the total number of moles of aldol condensation products.

Although hydrogen was present in the feed, since the catalyst had essentially no hydrogenation activity, less than 1.5%, and in most cases less than 0.5%, of the butanal fed was converted to the hydrogenated products butanol, 2-ethyl hexanal and 2-ethyl hexanol.

| Time (hrs) | Temp (° C.) | H$_2$ flow rate (ml/min) | Conversion (%) | Selectivity (%) | "enal"/ "aldol" (%) |
|---|---|---|---|---|---|
| 2 | 350 | 42 | 45 | 72 | 99 |
| 4 | 350 | 42 | 58 | 86 | 98 |
| 6 | 350 | 42 | 50 | 89 | 100 |
| 22 | 350 | 42 | 38 | 99 | 99 |
| 30 | 350 | 21 | 40 | 91 | 100 |
| 46 | 350 | 21 | 41 | 92 | 100 |
| 53 | 400 | 21 | 43 | 100 | 100 |
| 70 | 400 | 21 | 40 | 89 | 100 |
| 72 | 450 | 21 | 47 | 79 | 100 |

EXAMPLE 17

The procedure of Example 16 was repeated but using a catalyst containing 4% by weight of sodium and 0.1 % by weight of palladium obtained by the method described in Example 1 but including palladium nitrate in the aqueous solution used to impregnate the gel silica spheres. The results are shown in the following table.

| Time (hrs) | Temp (° C.) | H$_2$ flow rate (ml/min) | Conversion (%) | Selectivity (%) | "enal"/ "aldol" (%) |
|---|---|---|---|---|---|
| 4 | 350 | 50 | 82 | 81 | 30 |
| 6 | 350 | 50 | 58 | 92 | 14 |

-continued

| Time (hrs) | Temp (° C.) | H$_2$ flow rate (ml/min) | Conversion (%) | Selectivity (%) | "enal"/ "aldol" (%) |
|---|---|---|---|---|---|
| 8 | 350 | 50 | 49 | 94 | 7 |
| 24 | 350 | 50 | 42 | 100 | 5 |
| 31 | 350 | 25 | 39 | 96 | 7 |
| 48 | 350 | 25 | 34 | 100 | 11 |
| 55 | 400 | 25 | 40 | 86 | 12 |
| 72 | 400 | 25 | 32 | 92 | 16 |
| 77 | 450 | 25 | 38 | 75 | 25 |

The major aldol condensation product was 2-ethyl hexanal, but less than 2% of the butanal fed was hydrogenated to butanol and 2-ethyl hexanol, thus demonstrating the selective hydrogenation activity of palladium. By comparison with Example 16, it is seen that the conversion, although initially higher than that of Example 16, rapidly decreased indicating deactivation of the catalyst.

EXAMPLE 18

The procedure of Example 17 was repeated. After about 174 hours operation at 350° C. at a variety of pressures and hydrogen flow rates, by which time the conversion, at 5 bar and a hydrogen flow rate of 25 ml/min, had fallen to about 20% and the selectivity to about 52%, the catalyst was regenerated by replacing the flow of hydrogen and butanal by a mixture of 2% by volume oxygen and 98% by volume nitrogen at temperature of 350° C., a pressure of 5 bar gauge and at a rate of 100 ml/min for 6.5 hours. The reaction was re-commenced at the lower temperature of 300° C. at 5 bar gauge with a hydrogen flow rate of 50 ml/min. After two hours the conversion was about 48% but dropped to about 5% after 23 hours.

The catalyst was again regenerated by the above procedure for 6.5 hours and then the reaction re-commenced at the lower temperature of 250° C. at 5 bar gauge and a hydrogen flow rate of 50 ml/min. The conversion after 2 hours was about 15% but dropped to about 9% after 23 hours.

EXAMPLE 19

The procedure of Example 17 was repeated but using a catalyst containing 4% by weight of sodium as sodium oxide and 0.5% by weight of palladium made the same procedure as described above. The reaction was effected at 200° C. at a pressure of 5 bar gauge and a hydrogen flow rate of 50 ml/min. The conversion and selectivity dropped from about 36% and 84% respectively after 2 hours to about 9% and 52% respectively after 24 hours.

EXAMPLE 20

In this example, the aldol condensation of n-hexanal followed by hydrogenation was effected using a 3 ml bed of the catalyst of Example 3 crushed to a particle size of 0.6 to 1 mm, followed by a 3 ml bed of a copper oxide/zinc oxide hydrogenation catalyst made by co-precipitation and containing 35% by weight of copper oxide. This hydrogenation catalyst was likewise crushed to a particle size of 0.6 to 1 mm. Before commencing the testing, the hydrogenation catalyst was reduced in a current of dilute hydrogen (10% by volume of hydrogen in nitrogen) supplied at a rate of 50 ml/min at a pressure of 3 bar gauge at 140° C. over a period of 24 hours.

n-Hexanal and hydrogen were fed to the sodium oxide on silica catalyst which was maintained at 350° C. and then the reaction products fed through the hydrogenation catalyst which was maintained at 259° C. The initial conditions were a pressure of 3 bar gauge and a hydrogen flow rate of 85 ml/min and a n-hexanal flow rate of 0.05 ml/min. After various times on-line, samples of the products were analysed by mass spectroscopy and gas chromatography.

After 30 hours on-line, the pressure was increased to 5 bar gauge, and then to 7 bar gauge after 52 hours on-line. The hydrogen flow rate was decreased to 55 ml/min after 76 hours, to 42 ml/min after 155 hours, and to 22 ml/min after 179 hours. After a total of 203 hours on-line the experiment was stopped and the sodium on silica catalyst removed for analysis and found to contain about 4.2% by weight of carbon.

Throughout the experiment, all the n-hexanal reacted; the main products being n-hexanol and 2-butyl octanol. In the following table the conversions to n-hexanol and 2-butyl octanol respectively are calculated as Conv. hexanol=(moles of n-hexanol formed)×100/(moles of n-hexanal fed)

Conv. 2-butyloctanol=(2×moles of 2-butyl octanol formed)×100/(moles of n-hexanal fed)

| Time on-line (h) | Pressure (bar g) | $H_2$ flow rate (ml/min) | Conversion (%) to | |
|---|---|---|---|---|
| | | | n-hexanol | 2-butyl octanol |
| 6 | 3 | 85 | 22 | 32 |
| 24 | 3 | 85 | 35 | 35 |
| 30 | 3 | 85 | 43 | 32 |
| 47 | 5 | 85 | 43 | 31 |
| 52 | 5 | 85 | 50 | 25 |
| 76 | 7 | 85 | 63 | 19 |
| 107 | 7 | 55 | 58 | 21 |
| 155 | 7 | 55 | 65 | 17 |
| 162 | 7 | 42 | 60 | 28 |
| 179 | 7 | 42 | 60 | 18 |
| 186 | 7 | 22 | 48 | 28 |
| 203 | 7 | 22 | 38 | 28 |

What is claimed is:

1. A process for the production of unsaturated aldehydes by the aldol condensation of straight chain aldehydes by contacting the aldehyde in the vapour phase with a particulate catalyst comprising at least one basic alkali metal compound supported on an inert substrate at a temperature above 175° C.

2. A process according to claim 1 wherein the catalyst comprises a basic alkali metal compound supported on silica.

3. A process according to claim 1 wherein the catalyst comprises a basic alkali metal compound supported on alumina.

4. A process according to claim 1 wherein the catalyst contains 0.1–25% by weight of the alkali metal.

5. A process according to claim 1 wherein the inert substrate is in the form of particles having maximum and minimum dimensions in the range 0.5 to 10 mm and having a BET surface area in the range 50 to 500 $m^2/g$.

6. A process according to claim 1 wherein the reaction is effected at a temperature above 200° C.

7. A process according to claim 1 wherein the reaction is effected at a temperature in the range 200° C. to 350° C.

8. A process according to claim 1, wherein the aldehyde is a straight chain aldehyde containing 2 to 8 carbon atoms.

9. A process according to claim 8 wherein the aldehyde is propanal, butanal, or hexanal.

10. A process according to claim 1 wherein the product of the aldol condensation is partially hydrogenated to give a saturated aldehyde by means of a catalyst that has activity for the hydrogenation of carbon—carbon double bonds but does not hydrogenate carbonyl groups.

11. A process according to claim 1 wherein the product of the aldol condensation is hydrogenated to give an alcohol or mixture of alcohols.

12. A process according to claim 10 wherein the aldol condensation and hydrogenation are effected in a separate stages by passing the aldehyde through a bed of a particulate catalyst comprising at least one basic alkali metal compound supported on an inert substrate and that is free of components having hydrogenation activity, and then the reaction products are passed, together with hydrogen through a bed of a hydrogenation catalyst.

13. A process according to claim 1 wherein the particulate catalyst comprising at least one basic alkali metal compound supported on an inert substrate is periodically regenerated by heating in an oxygen-containing atmosphere.

14. A process according to claim 1, wherein the basic alkali metal compound is at least one of an oxide, hydroxide or carbonate of at least one of sodium, potassium, or cesium.

15. A process according to claim 14, wherein the inert support is carbon, silica, alumina, clay, silicalite or zeolite.

16. A process according to claim 2, wherein the alkali metal compound is a compound of sodium or potassium.

17. A process according to claim 16, wherein the catalyst contains from 0.4 to 18%, by weight, of the alkali metal.

* * * * *